(12) United States Patent
Fujita et al.

(10) Patent No.: US 7,715,891 B2
(45) Date of Patent: May 11, 2010

(54) RECEIVING APPARATUS CONTAINING PERFORMANCE INSPECTION FUNCTION OF ANTENNAS

(75) Inventors: Manabu Fujita, Tokyo (JP); Ayako Nagase, Tokyo (JP); Seiichiro Kimoto, Tokyo (JP); Toshiaki Shigemori, Tokyo (JP); Akira Matsui, Tokyo (JP); Kazutaka Nakatsuchi, Tokyo (JP)

(73) Assignee: Olympus Corporation, Tokyo (JP)

( * ) Notice: Subject to any disclaimer, the term of this patent is extended or adjusted under 35 U.S.C. 154(b) by 942 days.

(21) Appl. No.: 11/345,846

(22) Filed: Feb. 2, 2006

(65) Prior Publication Data

US 2006/0128337 A1    Jun. 15, 2006

Related U.S. Application Data

(63) Continuation of application No. PCT/JP2005/001776, filed on Feb. 7, 2005.

(30) Foreign Application Priority Data

Feb. 6, 2004    (JP) ............................. 2004-031002
Feb. 6, 2004    (JP) ............................. 2004-031003

(51) Int. Cl.
    *H04M 1/00*    (2006.01)
(52) U.S. Cl. ................. 455/575.7; 455/67.14; 343/751; 343/893; 600/118; 600/424
(58) Field of Classification Search ................. 455/424, 455/425, 456.5, 456.6, 561, 550.1, 575.1, 455/456.1, 41.1, 41.2, 67.11, 67.14, 575.7, 455/272, 277.1, 133; 600/110, 160, 424, 600/473, 309, 350, 593, 118, 476, 104, 302, 600/120; 348/77, 131; 382/286; 343/751, 343/893

See application file for complete search history.

(56) References Cited

U.S. PATENT DOCUMENTS

| | | | | |
|---|---|---|---|---|
| 4,960,106 | A | * | 10/1990 | Kubokawa et al. .......... 600/104 |
| 5,064,531 | A | | 11/1991 | Wang et al. |
| 6,208,287 | B1 | * | 3/2001 | Sikina et al. ................. 342/174 |
| 6,233,476 | B1 | * | 5/2001 | Strommer et al. ........... 600/424 |
| 6,904,308 | B2 | * | 6/2005 | Frisch et al. ................. 600/424 |
| 7,160,258 | B2 | * | 1/2007 | Imran et al. ................. 600/593 |
| 7,474,327 | B2 | * | 1/2009 | Davidson et al. .............. 348/77 |
| 2002/0105409 | A1 | * | 8/2002 | Nakamitsu et al. ........... 340/3.1 |
| 2003/0085994 | A1 | | 5/2003 | Fujita et al. |
| 2003/0174208 | A1 | * | 9/2003 | Glukhovsky et al. ........ 348/131 |
| 2003/0195396 | A1 | | 10/2003 | Scarantino et al. |

(Continued)

FOREIGN PATENT DOCUMENTS

| | | |
|---|---|---|
| JP | 11-225996 | 8/1999 |
| JP | 2001-231186 | 8/2001 |
| JP | 2003-135389 A | 5/2003 |

*Primary Examiner*—Duc Nguyen
*Assistant Examiner*—Charles Chow
(74) *Attorney, Agent, or Firm*—Scully, Scott, Murphy & Presser, P.C.

(57) ABSTRACT

A receiving apparatus which is used while connected to a plurality of antennas, the receiving apparatus receiving a radio signal through the antennas to perform a predetermined process to the received radio signal, the radio signal being transmitted from a body-insertable apparatus inserted into a subject, includes a receiving antenna selection unit that selects the antenna which is suitable for reception of the radio signal when the radio signal is transmitted from the body-insertable apparatus; a sequential antenna selection unit that sequentially selects each of the plurality of antennas when performance inspection of the plurality of antennas is performed; and a signal processing unit that performs a predetermined process to the radio signal received through the antenna, the antenna being selected by the receiving antenna selection unit or the sequential antenna selection unit.

7 Claims, 7 Drawing Sheets

U.S. PATENT DOCUMENTS

| | | | |
|---|---|---|---|
| 2004/0152988 A1* | 8/2004 | Weirich | 600/473 |
| 2004/0158138 A1* | 8/2004 | Kilcoyne et al. | 600/350 |
| 2004/0171915 A1* | 9/2004 | Glukhovsky et al. | 600/160 |
| 2004/0225184 A1* | 11/2004 | Shimizu et al. | 600/112 |
| 2004/0258328 A1* | 12/2004 | Adler | 382/286 |
| 2005/0004473 A1* | 1/2005 | Fujita et al. | 600/476 |
| 2006/0128337 A1* | 6/2006 | Fujita et al. | 455/277.1 |
| 2006/0202998 A1* | 9/2006 | Hirakawa et al. | 345/501 |
| 2006/0230108 A1* | 10/2006 | Tatsuta et al. | 709/204 |
| 2006/0241578 A1* | 10/2006 | Honda | 606/32 |
| 2007/0032697 A1* | 2/2007 | Shimizu et al. | 600/101 |
| 2007/0185382 A1* | 8/2007 | Shimizu et al. | 600/118 |
| 2008/0021281 A1* | 1/2008 | Fujimori | 600/160 |
| 2008/0045792 A1* | 2/2008 | Shimizu et al. | 600/118 |
| 2008/0188712 A1* | 8/2008 | Shimizu et al. | 600/118 |
| 2008/0200760 A1* | 8/2008 | Minai et al. | 600/117 |
| 2008/0255635 A1* | 10/2008 | Bettesh et al. | 607/60 |
| 2008/0294023 A1* | 11/2008 | Rabinovitz et al. | 600/309 |
| 2008/0306358 A1* | 12/2008 | Minai | 600/302 |
| 2009/0012360 A1* | 1/2009 | Kimoto et al. | 600/118 |
| 2009/0018395 A1* | 1/2009 | Honda | 600/118 |
| 2009/0054732 A1* | 2/2009 | Markham | 600/127 |
| 2009/0163771 A1* | 6/2009 | Kimoto et al. | 600/118 |
| 2009/0163772 A1* | 6/2009 | Koide et al. | 600/118 |

* cited by examiner

RECEIVING APPARATUS CONTAINING PERFORMANCE INSPECTION FUNCTION OF ANTENNAS

CROSS-REFERENCE TO RELATED APPLICATIONS

This application is a continuation of International Patent Application No. PCT/JP2005/001776, filed Feb. 7, 2005.

BACKGROUND OF THE INVENTION

1. Field of the Invention

The present invention relates to a receiving apparatus which is used while connected to plural antennas, the receiving apparatus receiving a radio signal through the antenna to perform a predetermined process to the received radio signal, the radio signal being transmitted from a body-insertable apparatus inserted into a subject.

2. Description of the Related Art

Recently, a swallowing type encapsulated endoscope makes its appearance in the field of an endoscope. The encapsulated endoscope is provided with an image pickup function and a wireless communication function. After the encapsulated endoscope is swallowed from a mouth of a patient for the purpose of observation (test), the encapsulated endoscope has the function of being moved in a body cavity, e.g., in organs such as a gaster and a small intestine according to peristaltic motion of the organ to sequentially take images until the encapsulated endoscope is naturally discharged from a human body.

The image data taken by the encapsulated endoscope in the body while the encapsulated endoscope is moved in the body cavity is sequentially transmitted to the outside by wireless communication, and the image data is received through a receiving antenna provided outside. Then, the data is reproduced by the receiving apparatus provided outside a subject based on the received radio signal, which allows the image in the body cavity of a patient to be obtained. Even after the patient swallows the encapsulated endoscope and before the encapsulated endoscope is discharged, the patient can freely move because the patient carries the receiving apparatus having the wireless communication function and a memory function. Then, a doctor or a nurse can make a diagnosis by displaying the organ image based on the image data stored in a memory (see Japanese Patent Application Laid-Open No. 2001-231186 (in particular, page 3 and FIG. 1)).

Because the encapsulated endoscope outputs the radio signal while sequentially moved in the body cavity, usually an encapsulated endoscope system has a configuration in which the plural receiving antennas are provided near the subject, e.g., on a subject surface, for receiving the radio signal outputted from the encapsulated endoscope. Therefore, in the conventional encapsulated endoscope system, the radio signal can be received by selecting the receiving antenna most suitable to the reception according to receiving intensity in each receiving antenna, usually by selecting the receiving antenna in which the receiving intensity is highest, and the image in the body cavity can be obtained while receiving sensitivity is kept good.

In the case where the receiving antenna does not perform the function due to a break of the receiving antenna and the like, the image in the body cavity taken by the encapsulated endoscope cannot be obtained. Accordingly, in the general encapsulated endoscope system, it is necessary that presence or absence of the break-down of the receiving antenna is confirmed at every predetermined period or before the encapsulated endoscope is inserted into a subject.

In a performance inspection of the receiving antennas, for example, the receiving apparatus is driven while equipped with the receiving antenna, and a dummy signal having a frequency equal to the radio signal transmitted from the encapsulated endoscope is transmitted to the receiving antenna. Because the transmitted dummy signal is inputted to the receiving apparatus through the receiving antenna, the presence or absence of the break-down of the receiving antenna is detected by determining whether a receiving level detected by the receiving apparatus is higher or lower than a predetermined threshold.

However, when the plural receiving antennas are provided outside the subject, the conventional encapsulated endoscope system has a problem that handling becomes complicated in the performance inspection of the receiving antennas. The problem will be described below.

As described above, the receiving apparatus switches the plural receiving antennas by selecting the receiving antenna having the highest receiving intensity. Accordingly, when the dummy signal is simultaneously transmitted to all the receiving antennas in the performance inspection of the receiving antennas, only the receiving intensity of the specific receiving antenna having the highest receiving intensity is monitored by the receiving apparatus, and the inspection cannot be performed for other receiving antennas except for the receiving antenna having the highest receiving intensity.

Therefore, in the conventional encapsulated endoscope system, it is necessary that the inspection is sequentially performed to the plural receiving antennas. That is, for example, it is necessary that an operation, in which the dummy signal is received for a single receiving antenna while the receiving antenna is arranged near an output antenna for outputting the dummy signal, is sequentially performed to each receiving antenna. Accordingly, when the inspection is performed to the plural receiving antennas, the process becomes very complicated.

SUMMARY OF THE INVENTION

A receiving apparatus according to one aspect of the present invention is used while connected to a plurality of antennas, and receives a radio signal through the antennas to perform a predetermined process to the received radio signal. The radio signal is transmitted from a body-insertable apparatus inserted into a subject. The receiving apparatus includes a receiving antenna selection unit that selects the antenna which is suitable for reception of the radio signal when the radio signal is transmitted from the body-insertable apparatus; a sequential antenna selection unit that sequentially selects each of the plurality of antennas when performance inspection of the plurality of antennas is performed; and a signal processing unit that performs a predetermined process to the radio signal received through the antenna, the antenna being selected by the receiving antenna selection unit or the sequential antenna selection unit.

A receiving apparatus according to another aspect of the present invention is used while connected to a plurality of antennas, and receives a radio signal through the antenna to perform a predetermined process to the received radio signal. The radio signal being transmitted from a body-insertable apparatus inserted into a subject. The receiving apparatus includes a receiving antenna selection unit that selects the antenna which is suitable for reception of the radio signal from the plurality of antennas when the radio signal is transmitted from the body-insertable apparatus; an inspection signal generation unit that generates an inspection radio signal when the performance inspection is performed to the plurality of antennas; a transmitting antenna selection unit that selects the antenna which transmits the inspection radio signal from the plurality of antennas when performance inspection is performed to the plurality of antennas; and a receiving antenna sequential selection unit that sequentially selects the plurality of antennas except for the antenna which is selected by the transmitting antenna selection unit when the performance inspection is performed to the plurality of antennas.

A receiving apparatus according to still another aspect of the present invention is used while connected to a plurality of antennas, and receives a radio signal through the antenna to perform a predetermined process to the received radio signal. The radio signal is transmitted from a body-insertable apparatus inserted into a subject. The receiving apparatus includes a signal processing unit that performs a predetermined process to the radio signal received through the antenna; a recording unit that outputs the received radio signal to a recording medium when the radio signal is transmitted from the body-insertable apparatus, and subjected to the predetermined process by the signal processing unit; and a real-time output unit that outputs an inspection radio signal in real time when performance inspection of the plurality of antennas is performed, the inspection radio signal being transmitted from the outside and being received through the antenna, and subjected to the predetermined process by the signal processing unit.

A receiving apparatus according to still another aspect of the present invention is used while connected to a plurality of antennas, and receives a radio signal through the antenna to perform a predetermined process to the received radio signal. The radio signal is transmitted from a body-insertable apparatus inserted into a subject. The receiving apparatus includes a signal processing unit that performs a predetermined process to the radio signal received through the antenna; a recording unit that outputs the received radio signal to a recording medium when the radio signal is transmitted from the body-insertable apparatus, and subjected to the predetermined process by the signal processing unit; and a real-time display unit that displays received contents of an inspection radio signal in each of the antennas in real time when performance inspection of the plurality of antennas is performed, the inspection radio signal being transmitted from the outside and being received through the antenna.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

A receiving apparatus and a wireless intra-subject information obtaining system, which are of the best mode for carrying out the invention, will be described below. It should be noted that all the drawings are schematic only and elements shown therein may in practice have different thickness and width, and parts thereof may in practice have different ratios in thickness, and it is also obvious that the drawings may include elements shown in different dimensions or ratios.

A receiving apparatus according to a first embodiment will be described below. The receiving apparatus according to the first embodiment has the function of receiving the radio signal, outputted from the body-insertable apparatus which is inserted into the subject to perform the predetermined function in the subject, through a receiving antenna and of performing the predetermined signal processing to the received radio signal. Further, during the performance inspection of the receiving antenna, while the receiving apparatus according to the first embodiment has the function of appropriately selecting the receiving antenna, the receiving apparatus has the function of performing the predetermined process to the radio signal received through the selected receiving antenna. A configuration of the receiving apparatus according to the first embodiment will be described and then each function will be described with reference to the drawings.

Figure 1:
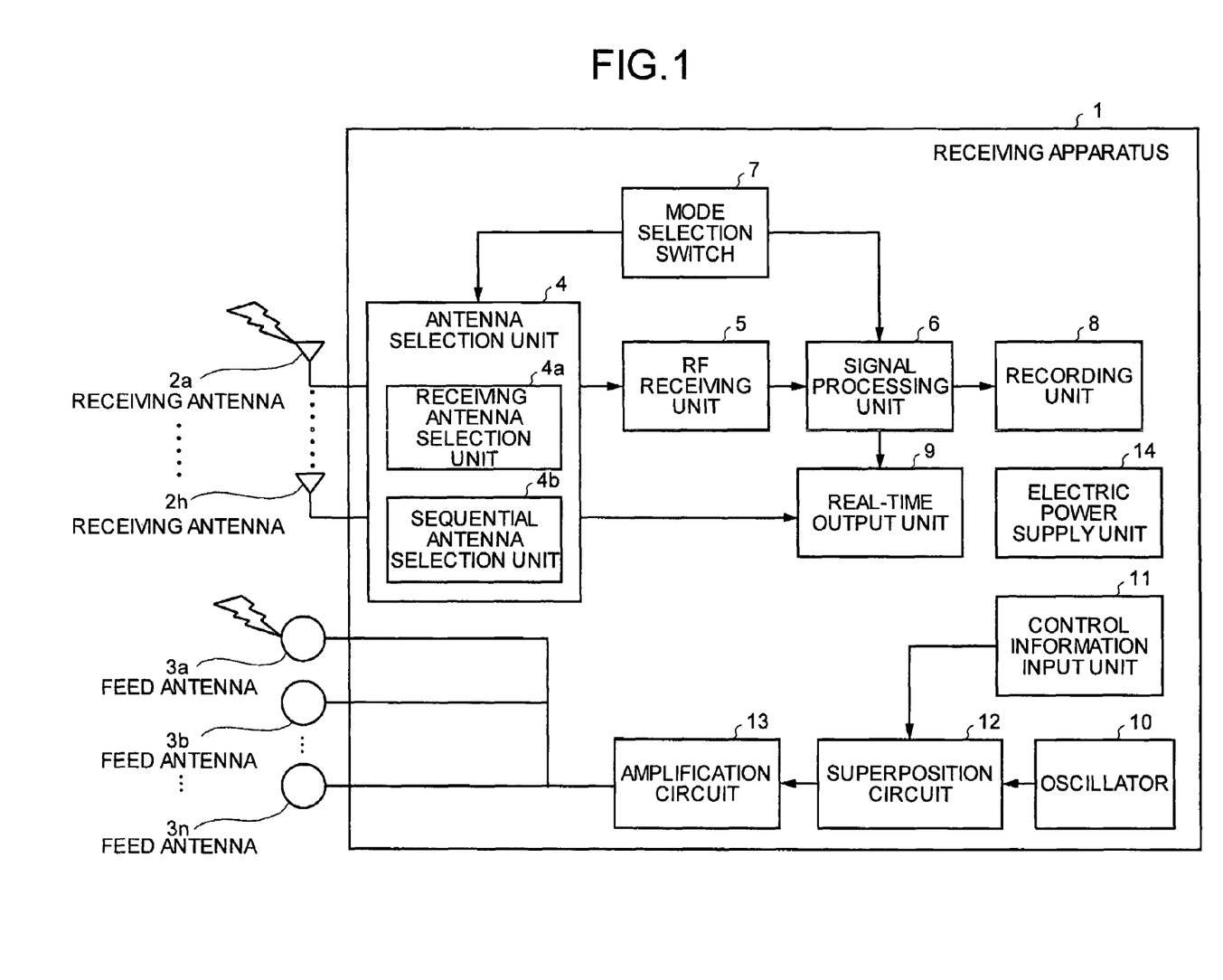
FIG. 1 is a block diagram showing an entire configuration of a receiving apparatus according to a first embodiment.

FIG. 1 is a block diagram showing a configuration of the receiving apparatus according to the first embodiment. As shown in FIG. 1, a receiving apparatus 1 according to the first embodiment is used while connected to receiving antennas 2a to 2h and feed antennas 3a to 3n.

The receiving antennas 2a to 2h function as an example of the antenna in claims. Specifically the receiving antennas 2a to 2h are used while electrically connected to the receiving apparatus 1. The receiving antennas 2a to 2h are arranged on a surface of a subject body in use, and the receiving antennas 2a to 2h are to receive the radio signal transmitted from the body-insertable apparatus while the body-insertable apparatus is inserted in the subject. Specifically, for example, each of the receiving antennas 2a to 2h includes a loop antenna, fixing means for fixing the loop antenna to the subject, and a capacitor which forms a resonance circuit between the loop antenna. The first embodiment includes eight receiving antennas 2a to 2h by way of example. However, the number of receiving antennas 2 is not particularly limited, and an arbitrary number of receiving antennas 2 may be used as long as the number of receiving antennas 2 is at least two.

Similarly to the receiving antennas 2a to 2h, the feed antennas 3a to 3n are used while electrically connected to the receiving apparatus 1. Specifically the feed antennas 3a to 3n transmit the radio signal generated in the receiving apparatus 1 to the body-insertable apparatus, and the feed antennas 3a to 3n have the function of feeding electric power for driving and the like to the body-insertable apparatus.

Then, the configuration of the receiving apparatus 1 will be described. As shown in FIG. 1, the receiving apparatus 1 includes an antenna selection unit 4, an RF receiving unit 5, a signal processing unit 6, and a mode selection switch 7. The antenna selection unit 4 includes a receiving antenna selection unit 4a and a sequential antenna selection unit 4b, and the antenna selection unit 4 selects any one of the receiving antennas 2a to 2h connected to the receiving apparatus 1. The RF receiving unit 5 performs a demodulation process and the like to the radio signal which is received through the receiving antenna 2 selected by the antenna selection unit 4. The signal processing unit 6 performs a predetermined process to the signal to which the demodulation process and the like are performed. The mode selection switch 7 switches an operation mode of the antenna selection unit 4 and the signal processing unit 6. The receiving apparatus 1 also includes a recording unit 8 and a real-time output unit 9 which outputs the signal processed by signal processing unit 6 to the outside.

The antenna selection unit 4 selects any one of the receiving antennas 2a to 2h. Specifically the antenna selection unit 4 has the configuration in which the receiving antenna selection unit 4a and sequential antenna selection unit 4b included therein are appropriately switched according to an operation mode.

The receiving antenna selection unit 4a selects the proper receiving antenna from the receiving antennas 2a to 2h when the receiving apparatus performs the receiving operation of the radio signal transmitted from the body-insertable apparatus. As described later, while the receiving antennas 2a to 2h are fixed to the subject, the body-insertable apparatus is sequentially moved in the subject. Accordingly, the receiving antenna 2 suitable to receive the radio signal is sequentially changed among the plural receiving antennas 2a to 2h.

Therefore, in order that the receiving apparatus 1 according to the first embodiment can always receive the radio signal through the optimum receiving antenna 2 for the body-insertable apparatus, the receiving antenna is selected from the receiving antennas 2a to 2h by the receiving antenna selection unit 4a. Specifically the receiving antenna selection unit 4a has the function of comparing radio signal intensities received through the receiving antennas 2a to 2h to one another. The receiving antenna selection unit 4a also has the function of selecting the receiving antenna 2, which receives the radio signal having the highest intensity, to output the radio signal received through the selected receiving antenna 2 to the RF receiving unit 5. For the operation algorithm of the receiving antenna selection unit, in addition to the intensity comparison, it is also possible that the receiving antenna 2 arranged nearest the body-insertable apparatus is selected by using a body-insertable apparatus position detection mechanism, and it is also possible that other algorithms are used.

The sequential antenna selection unit 4b sequentially selects the receiving antennas 2a to 2h when performance inspections of the receiving antennas 2a to 2h are performed. Specifically the sequential antenna selection unit 4b has the function of sequentially performing the selection of the receiving antenna 2 by the algorithm different from that of the receiving antenna selection unit 4a. More specifically the sequential antenna selection unit 4b has the function of sequentially selecting one receiving antenna 2 with respect to the receiving antennas 2a to 2h irrespective of the received radio signal intensities, and the sequential antenna selection unit 4b also has the function of outputting identification information on the selected receiving antenna 2 to the real-time output unit 9 while outputting the radio signal received by the selected receiving antenna 2 to the RF receiving unit 5.

The mode selection switch 7 switches the operation mode of the receiving apparatus 1 between a receiving processing operation of the radio signal transmitted from the body-insertable apparatus and a performance inspection operation of the receiving antennas 2a to 2h. Specifically the mode selection switch 7 has the configuration in which the operation mode is inputted by a user, and the mode selection switch 7 has the function of outputting the inputted operation mode information to the antenna selection unit 4 and the signal processing unit 6. According to the operation mode outputted by the mode selection switch 7, the antenna selection unit 4 switches between the receiving antenna selection unit 4a and the sequential antenna selection unit 4b, and the signal processing unit 6 switches the output between the recording unit 8 and the real-time output unit 9.

The recording unit 8 stores predetermined information generated based on the radio signal which is transmitted from the body-insertable apparatus and received through the receiving antennas 2a to 2h, e.g., a body cavity image. Specifically the recording unit 8 has the function of outputting data to a later-described portable recording medium 18.

The real-time output unit 9 outputs the signal, received through the receiving antenna which is an inspection object, in real time during the performance inspection of the receiving antennas 2a to 2h. Specifically the real-time output unit 9 has the configuration in which the radio signal processed by the signal processing unit 6 and the antenna selection information from the antenna selection unit 4 are inputted thereto, and the real-time output unit 9 has the function of outputting these pieces of information to the outside in real time.

In addition to the above receiving mechanism, the receiving apparatus 1 according to the first embodiment has the function of generating the radio signal transmitted to the body-insertable apparatus through the feed antennas 3a to 3n. In order to realize the above functions, the receiving apparatus 1 according to the first embodiment includes an oscillator 10, a control information input unit 11, a superposition circuit 12, and an amplification circuit 13. The oscillator 10 generates feed signal and regulates an oscillating frequency of the radio signal to transmit. The control information input unit 11 generates a control information signal by inputting control information for controlling the drive of the body-insertable apparatus. The superposition circuit 12 superposes the feed signal and the control signal. The amplification circuit 13 amplifies the superposed signal. The signal amplified by the amplification circuit 13 is sent to the feed antennas 3a to 3n and transmitted to an encapsulated endoscope 16 through the feed antennas 3a to 3n.

The receiving apparatus 1 further includes an electric power supply unit 14 for driving the above components. The electric power supply unit may be configured so as to incorporate a storage battery or the like therein to distribute the electric power to the components, or the electric power supply unit may includes only the configuration in which the electric power supplied from the storage battery or the like provided outside is distributed to the components.

Figure 2:
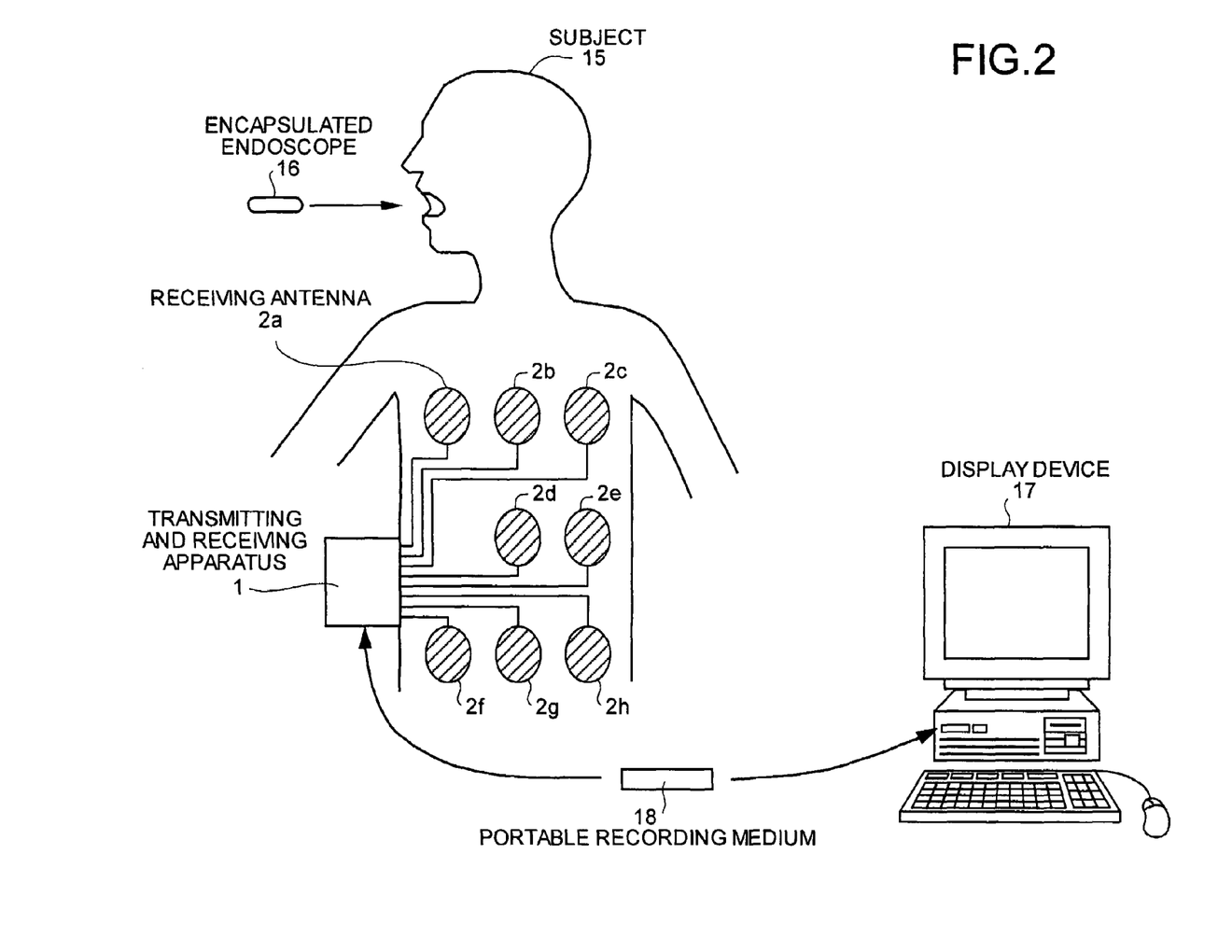
FIG. 2 is a schematic view showing an entire configuration of an intra-subject information obtaining system in which the receiving apparatus according to the first embodiment is used.

Then, the intra-subject information obtaining system which is formed by using the receiving apparatus 1 will be described. FIG. 2 is a schematic view showing a configuration and a state of use of the intra-subject information obtaining system including the receiving apparatus according to the first embodiment. As shown in FIG. 2, in the intra-subject information obtaining system, the receiving apparatus 1 is used while attached to a subject 15, and the receiving antennas 2a to 2h connected to the receiving apparatus 1 are used while separated from one another at predetermined intervals and applied to the body surface of the subject 15. Similarly to the receiving antennas 2a to 2h, the feed antennas 3a to 3n (not shown in FIG. 2) are also used while applied to the body surface of the subject 15. In addition to the above components, the intra-subject information obtaining system also includes the encapsulated endoscope 16, a display device 17, and a portable recording medium 18. The encapsulated endoscope 16 is an example of the body-insertable apparatus which is inserted into the subject 15. The display device 17 displays the image in the subject 15 taken by the encapsulated endoscope 16. The portable recording medium 18 is for passing information between the receiving apparatus 1 and the display device 17.

The encapsulated endoscope 16 functions as the body-insertable apparatus inserted into the subject 15. The encapsulated endoscope 16 is configured to include predetermined function performing means such as an image pickup device which takes the image of the inside of the subject 15 and wireless transmission means for transmitting the information on the subject 15, obtained by the predetermined function performing means, to the outside. As described above, the first embodiment has the configuration in which the receiving apparatus 1 generates the radio signal including the feed signal and transmits the radio signal through the feed antennas 3a to 3n in the wireless manner, therefore the first embodiment has a receiving mechanism for receiving the feed signal, an electric power mechanism for reproducing the received feed signal in the form the electric power, and a battery mechanism for accumulating the reproduced electric power.

The display device 17 displays the image in the subject 15 obtained by the encapsulated endoscope 16 or the like, and the display device 17 has the configuration in which the image is displayed based on the data supplied through the portable recording medium 18 like a workstation. Specifically the display device 17 may be configured to directly display the image with a CRT display, a liquid crystal display, or the like, or the display device 17 may be configured to output the image to other mediums such as a printer.

The portable recording medium 18 is detachable from the receiving apparatus 1 and the display device 17, and the portable recording medium 18 has a structure that the information can be outputted and recorded when the portable recording medium 18 is loaded into the receiving apparatus 1 and the display device 17. Specifically, when the encapsulated endoscope 16 is moved in the body cavity of the subject 15, the portable recording medium 18 records the information on a position of the encapsulated endoscope 16 while loaded into the receiving apparatus 1. Specifically the portable recording medium 18 is loaded into the recording unit 8 included in the receiving apparatus 1, and the portable recording medium 18 obtains the information through the recording unit 8. After the encapsulated endoscope 16 is discharged from the subject 15, the portable recording medium 18 is taken out from the receiving apparatus 1 and loaded into the display device 17, and the recorded data is read by the display device 17. The data passing between the receiving apparatus 1 and the display device 17 is performed by the portable recording medium 18 such as a compact flash (registered trademark) memory, which allows the subject 15 to act freely even when the encapsulated endoscope 16 is moved in the subject 15 unlike in the case where the receiving apparatus 1 and the display device 17 are connected by a cable.

An operation of the intra-subject information obtaining system shown in FIG. 2 will briefly be described. As shown in FIG. 2, the encapsulated endoscope 16 which is one of modes of the body-insertable apparatus is inserted into the subject 15 through a mouth of the subject 15. Since the encapsulated endoscope 16 is sequentially moved to an esophagus, the gaster, the small intestine, and a large intestine from an oral cavity after inserted into the subject 15, the encapsulated endoscope 16 obtains the image data of each region in the subject 15 according to the movement of the encapsulated endoscope 16 to generate the radio signal including the obtained image data (image signal), and the encapsulated endoscope 16 transmits the generated radio signal to the outside of the subject 15.

The transmitted radio signal is received through any one of the receiving antennas 2a to 2h connected to the receiving apparatus 1. In the receiving apparatus 1, the mode selection switch 7 drives the receiving antenna selection unit 4a included in the antenna selection unit 4 to select the receiving antenna through which receiving intensity of the radio signal transmitted from the encapsulated endoscope 16 is highest among the receiving antennas 2a to 2h. The radio signal is outputted in the order of the RF receiving unit 5 and the signal processing unit 6 through the selected receiving antenna 2. Since the signal processing unit 6 switches to redirect the output to the recording unit 8 by the control of the mode selection switch 7, the signal of which the predetermined process is finished by the signal processing unit 6 is recorded in the portable recording medium 18 through the recording unit 8.

The above operation by the receiving apparatus 1 is repeatedly performed until the encapsulated endoscope 16 is discharged outside the subject 15. After the encapsulated endoscope 16 is discharged outside the subject 15, the portable recording medium 18 is taken from the receiving apparatus 1 and loaded to the display device 17. As a result of the repeated operation of the receiving apparatus 1, the image data of the region where the encapsulated endoscope 16 passes through is stored in the portable recording medium 18. Accordingly, the display device 17 reads the image data recorded in the portable recording medium 18 to visually display the image in the body cavity of the subject 15. Thus, the operation of the intra-subject information obtaining system is completed.

Then, the performance inspection of the receiving antennas 2a to 2h using the receiving apparatus 1 of the first embodiment will be described. As described above, the receiving antennas 2a to 2h are required to receive the radio signal transmitted from the encapsulated endoscope 16 which is the body-insertable apparatus. When the receiving antennas 2a to 2h do not exert the function due to a break in the receiving antennas 2a to 2h and the like, the insertion of the encapsulated endoscope 16 into the subject 15 obtains no piece of information. Therefore, in the usual intra-subject information obtaining system, the performance inspection of the receiving antennas 2a to 2h is performed before the encapsulated endoscope 16 is inserted into the subject 15. When it is confirmed that the receiving antennas 2a to 2h function normally, the intra-subject information obtaining system is used.

Figure 3:
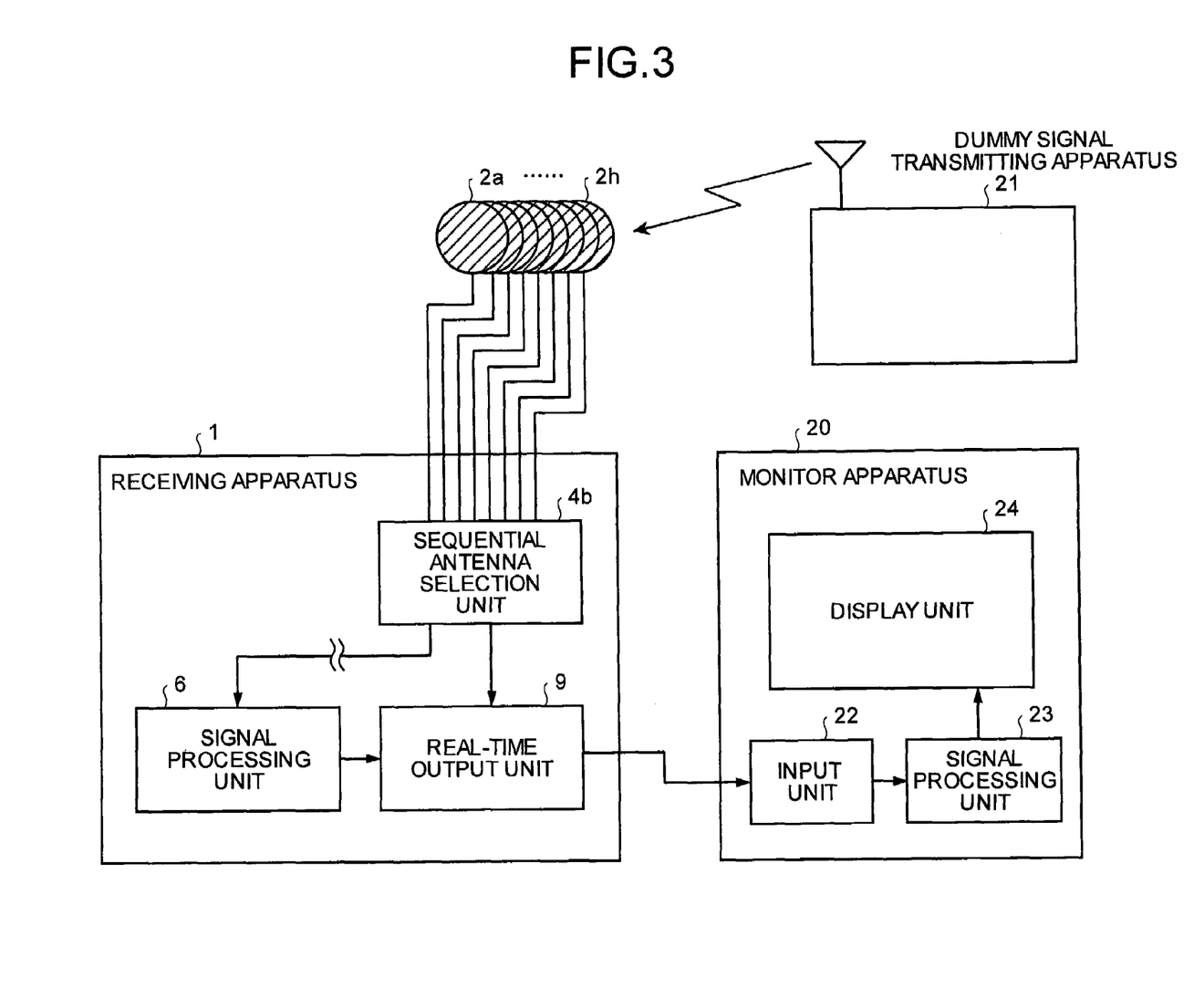
FIG. 3 is a block diagram showing an entire configuration of an example of an inspection system in which the receiving apparatus according to the first embodiment is used.

FIG. 3 is a schematic view showing the configuration of an inspection system and an inspection mode of the performance inspection of the receiving antennas 2a to 2h. Specifically, as shown in FIG. 3, the inspection system includes the receiving apparatus 1 connected to the antennas 2a to 2h, a monitor apparatus 20 connected to the receiving apparatus 1, and a dummy signal transmitting apparatus 21 transmitting an inspection dummy signal to the receiving antennas 2a to 2h.

As described above, when the performance inspection of the receiving antennas 2a to 2h is performed, the sequential antenna selection unit 4b is driven based on an instruction of the mode selection switch 7, and the signal processing unit 6 switches to redirect the output to the real-time output unit 9. Accordingly, as shown in FIG. 3, in the performance inspection, the receiving antennas 2a to 2h are connected to the sequential antenna selection unit 4b, and the signal processing unit 6 outputs the generated data to the real-time output unit 9.

The monitor apparatus 20 displays the data outputted from the real-time output unit 9. Specifically the monitor apparatus 20 includes an input unit 22, a signal processing unit 23, and a display unit 24. The input unit 22 receives the data outputted from the real-time output unit 9 as an input. The signal processing unit 23 performs the predetermined process to the inputted data to output the displayable image data. The display unit 24 displays the data outputted from the signal processing unit 23. The display unit 24 is for displaying the data outputted from the signal processing unit 23. A dedicated apparatus for the use of the performance inspection of the receiving antennas 2a to 2h may be used as the monitor apparatus 20, or alternatively, a general apparatus such as a personal computer may be used as the monitor apparatus 20.

The dummy signal transmitting apparatus 21 functions as inspection signal transmitting means for transmitting dummy signals, which are the inspection radio signal, to the receiving antennas 2a to 2h in the performance inspection. Any signal can be used as the dummy signal transmitted from the dummy signal transmitting apparatus 21 as long as the signal has a particular pattern distinguished from a noise. In the first embodiment, similarly to the radio signal transmitted from the encapsulated endoscope 16, the radio signal including a fixed pattern signal showing an image shall be used as the dummy signal in the performance inspection. More preferably the dummy signal shall include the image data similar to the image having the same contents as the image transmitted from the encapsulated endoscope 16, i.e., the image in the body cavity. Accordingly, in the first embodiment, the display unit 24 included in the monitor apparatus 20 displays the information for identifying the receiving antenna through which the radio signal is received along with the predetermined image pattern. The dummy signal transmitting apparatus 21 may not be independently provided while separated from the encapsulated endoscope 16, but the encapsulated endoscope 16 may be caused to function as the dummy signal transmitting apparatus 21. Also the encapsulated endoscope (not shown) including the dummy signal transmitting function which is provided while separated from the encapsulated endoscope 16 may be used as the dummy signal transmitting apparatus 21 to perform the performance inspection of the receiving antenna.

The operation of the inspection system will be described. As shown in FIG. 3, in the performance inspection, the receiving antennas 2a to 2h are arranged while collected up at one position, and all the receiving antennas 2a to 2h are arranged while being able to receive the dummy signal transmitted from the dummy signal transmitting apparatus 21. On the other hand, in the receiving apparatus 1, the sequential antenna selection unit 4b is driven to sequentially select the receiving antennas 2a to 2h. For example, the sequential antenna selection unit 4b selects the receiving antenna 2a from the receiving antennas 2a to 2h to output the received dummy signal to the RF receiving unit 5 through the receiving antenna 2a. After the process in the RF receiving unit 5, the predetermined signal processing is performed by the signal processing unit 6, and the signal is outputted to the real-time output unit 9.

The sequential antenna selection unit 4b also outputs identification information on the receiving antenna 2a being selected by the sequential antenna selection unit 4b to the real-time output unit 9. Accordingly, the signal corresponding to contents of the dummy signal received through the receiving antenna 2a and the identification-information indicating that the receiving antenna 2a is selected by the sequential antenna selection unit 4b are inputted to the real-time output unit 9, and the real-time output unit 9 outputs the signal and the identification information to the monitor apparatus 20 while the signal and the identification information are synthesized. The signal outputted through the real-time output unit 9 is inputted to monitor apparatus 20 through the input unit 22, and the signal is displayed by the display unit 24 after processed by the signal processing unit 23. As described above, since the received dummy signal and the identification information on the receiving antenna 2a used in receiving the dummy signal are included in the data outputted from the real-time output unit 9, the image according to the received dummy signal and the data that the image is received through the receiving antenna 2a are displayed in the display unit 24.

Since the sequential antenna selection unit 4b has the function of sequentially selecting the receiving antennas 2a to 2h irrespective of the receiving intensity, after the performance inspection of the receiving antenna 2a is finished, the performance inspection similar to the above contents is sequentially performed for the receiving antennas 2b, 2c, . . . . Therefore, in the inspection system shown in FIG. 3, the performance inspection is surely performed for all the receiving antennas 2a to 2h without generating inspection dropout with respect to the receiving antenna 2.

For example, when the receiving antenna 2 in the performance inspection is selected in such the conventional way that the antenna selection algorithm similar to the reception of the radio signal from the body-insertable apparatus is used, only the receiving antenna 2 having the highest receiving intensity is selected and other receiving antennas 2 are not selected, which results in the problem that the performance inspection is not sufficiently performed. However, in the receiving apparatus 1 according to the first embodiment, the antenna selection unit 4 includes the sequential antenna selection unit 4b which is driven in the performance inspection, so the antenna selection is sequentially performed irrespective of the receiving intensity of each receiving antenna 2 in the performance inspection. Accordingly, as shown in FIG. 3, even if all the receiving antennas 2a to 2h are arranged while being able to receive the dummy signal transmitted from the dummy signal transmitting apparatus 21, the performance inspection can surely be performed for all the receiving antennas 2a to 2h. Therefore, unlike the conventional art, it is not necessary that an inspector sequentially brings each of the receiving antennas 2a to 2h close to the dummy signal transmitting apparatus 21 to perform the performance inspection, and the performance inspection can be performed simply and rapidly.

The receiving apparatus 1 according to the first embodiment is not only used as a part of the intra-subject information obtaining system shown in FIG. 2, but also has the function of performing the predetermined process to the received radio signal in the performance inspection. Accordingly, in the performance inspection, it is not necessary to separately prepare the apparatus having the signal processing function, and the inspection system can be constructed by the simple configuration. Further, the receiving apparatus 1 is also configured to be used in the performance inspection, which results in the advantage that the performance inspection of the receiving antennas 2a to 2h becomes practical one reflecting the actual use mode.

In the receiving apparatus 1 according to the first embodiment, the dummy signal includes the image data, and the image corresponding to the dummy signal received through any one of the receiving antennas 2a to 2h is displayed in the display unit 24. Therefore, the inspector can visually comprehend the receiving status through each of the receiving antennas 2a to 2h in the performance inspection.

Particularly, when the image data included in the dummy signal is the data concerning the previously taken image in the subject 15, the performance inspection becomes more practical. In the case of the completely broken receiving antenna 2, it is easily possible to determine that the receiving antenna 2 breaks down because the image is not displayed in the display unit 24. However, for example, in the case where the relatively clear image is displayed on the display unit 24 while the image is not in the ideal state, it is not easy to determine that the receiving antenna 2 breaks down at which level. In the case the use of the dummy signal including the image data corresponding to the image in the subject, for example, a doctor or a nurse can easily determine whether the receiving status is in a level affecting diagnosis or not by seeing the image displayed in the display unit 24.

The receiving apparatus 1 according to the first embodiment adopts the configuration in which the signal processed by the signal processing unit 6 is outputted to the outside not through the recording unit 8 but through the real-time output unit 9 in the performance inspection of the receiving antennas 2a to 2h. Therefore, the inspector can confirm the performance inspection result in real time. For example, when the performance inspection is performed immediately before the encapsulated endoscope 16 is inserted into the subject 15, the performance inspection can rapidly be performed. Since the receiving apparatus 1 and the receiving antennas 2a to 2h are not attached to the subject 15 in performing the performance inspection, the problem that a degree of freedom is restricted in activity of the subject 15 is not generated, even if the receiving apparatus 1 is connected to the external apparatus in real time.

Figure 4:
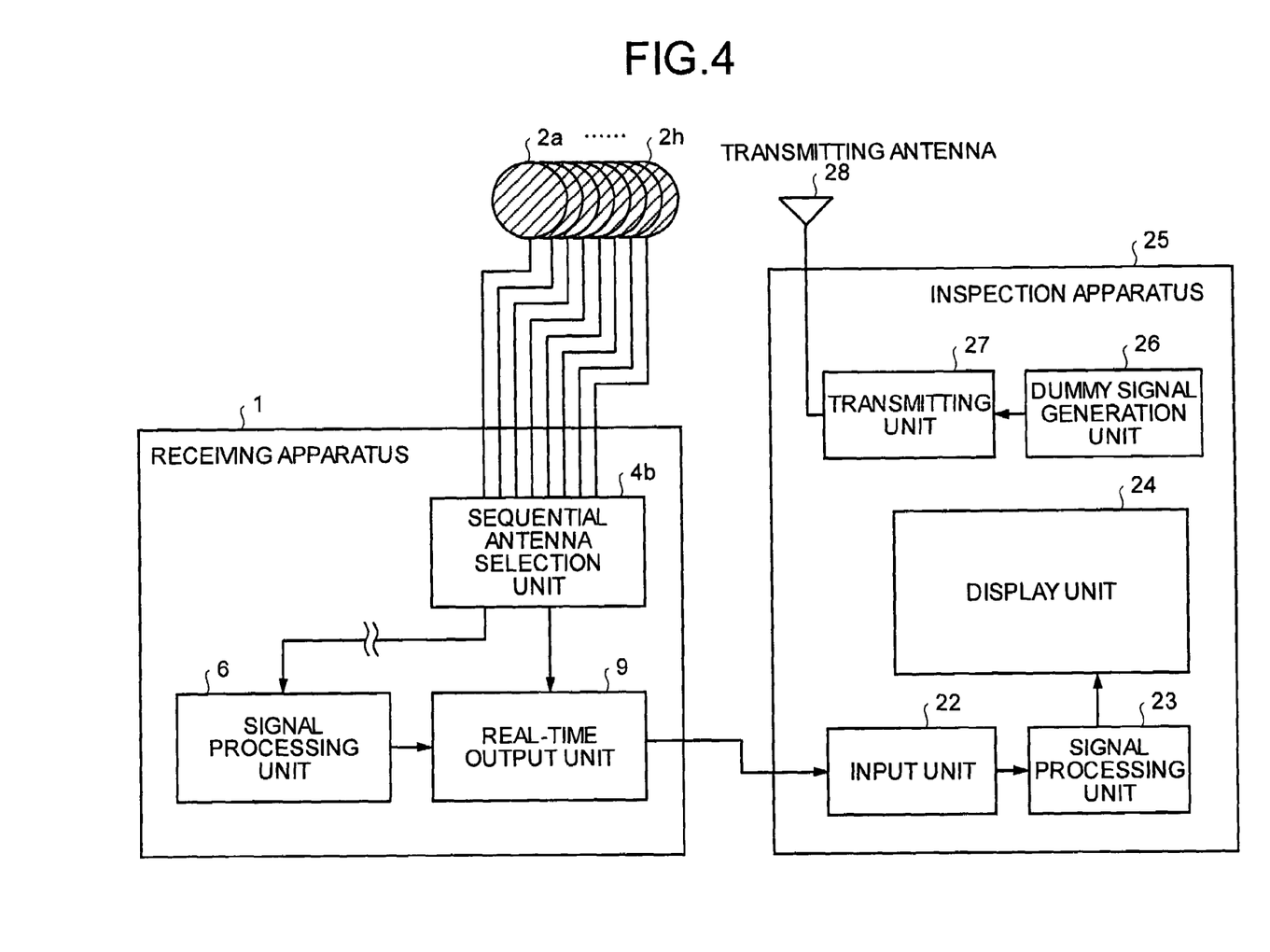
FIG. 4 is a block diagram showing an entire configuration of another example of the inspection system in which the receiving apparatus according to the first embodiment is used.

The monitor apparatus 20 and the dummy signal transmitting apparatus 21 may be integrally configured in the inspection system which inspects the performance of the receiving antennas 2a to 2h. That is, as shown in FIG. 4, the inspection system can be formed by using an inspection apparatus 25 including the input unit 22, the signal processing unit 23, the display unit 24, and a mechanism for transmitting the dummy signal. The mechanism includes a dummy signal generation unit 26, a transmitting unit 27, and a transmitting antenna 28. When the above configuration is adopted, apparatus handling is simplified in the performance inspection, so the performance inspection of the receiving antennas 2a to 2h can be performed more simply and rapidly.

A receiving apparatus according to a second embodiment will be described. The receiving apparatus according to the second embodiment has a configuration in which the mechanism required in the performance inspection of the receiving antennas 2a to 2h is included in the receiving apparatus. For example, the receiving apparatus has the configuration in which the performance inspection of the receiving antennas 2a to 2h can be performed while the receiving apparatus is operated as a part of the intra-subject information obtaining system.

Figure 5:
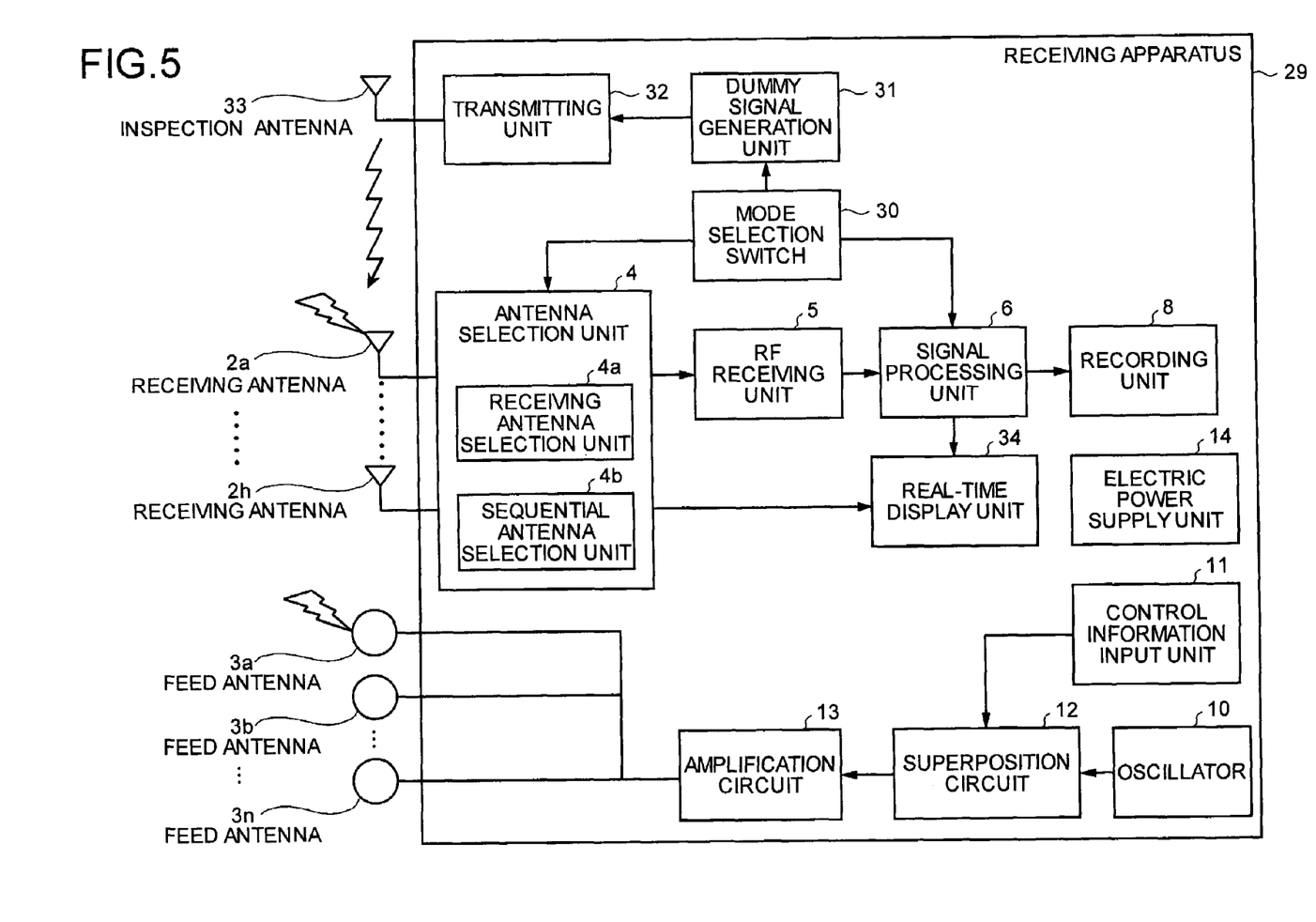
FIG. 5 is a block diagram showing an entire configuration of a receiving apparatus according to a second embodiment.

FIG. 5 is a block diagram showing a configuration of the receiving apparatus according to the second embodiment. As shown in FIG. 5, the same numeral and name as the first embodiment are used for the component in common with the first embodiment, and the component has the same configuration and function as the first embodiment unless described otherwise below.

A receiving apparatus 29 according to the second embodiment includes a mode selection switch 30 instead of the mode selection switch 7 of the first embodiment, and the receiving apparatus 29 also includes a real-time display unit 34 which performs the display operation in real time instead of the real-time output unit 9. In addition to the configuration of the receiving apparatus 1 according to the first embodiment, the receiving apparatus 29 according to the second embodiment includes a dummy signal generation unit 31, a transmitting unit 32, and an inspection antenna 33. The dummy signal generation unit 31 generates the dummy signal. The transmitting unit 32 performs a modulation process and the like to the generated dummy signal. The inspection antenna 33 performs the wireless transmission of the processed dummy signal to the receiving antennas 2a to 2h. The real-time display unit 34 may display the image like the display unit 24 of the first embodiment. However, in the second embodiment, in order to suppress upsizing of the receiving apparatus 29, the real-time display unit 34 shall include a mechanism which determines the performance inspection result based on the signal outputted from the signal processing unit 6 and LED or the like which displays a pattern corresponding to the determined result. The mode selection switch 30 has the function of outputting the information on the operation mode of the receiving apparatus 29 not only to the antenna selection unit 4 and the signal processing unit 6 but also to the dummy signal generation unit 31.

The advantage generated by providing the components corresponding to the monitor apparatus 20 and dummy signal transmitting apparatus 21 of the first embodiment in the receiving apparatus 29 will be described. As described above, since the receiving antennas 2a to 2h perform the major function when the body-insertable apparatus such as the encapsulated endoscope 16 is inserted into the subject 15, it is necessary to previously inspect the performance of the receiving antennas 2a to 2h.

However, when the receiving apparatus is used as a part of the intra-subject information obtaining system, there is an undeniable possibility that the break of the receiving antennas 2a to 2h is generated. Particularly, as shown in FIG. 2, since the receiving antennas 2a to 2h is used while fixed onto the body surface of the subject 15, forced stress is applied to the receiving antennas 2a to 2h depending on the movement of the subject 15, there is the possibility that the trouble such as the break is generated after the use of the receiving apparatus is started as a part of the intra-subject information obtaining system even if the receiving apparatus has no problem before the use of the receiving apparatus.

Therefore, the receiving apparatus according to the second embodiment adopts the configuration in which the components corresponding to the monitor apparatus 20 and dummy signal transmitting apparatus 21 of the first embodiment are included in the receiving apparatus. Therefore, the receiving apparatus 29 can perform the performance inspection of the receiving antennas 2a to 2h while the receiving apparatus 29 is used as a part of the intra-subject information obtaining system.

In the case where the receiving apparatus 29 is used as a part of the intra-subject information obtaining system, basically the receiving antennas 2a to 2h is used in order to receive the radio signal transmitted from the encapsulated endoscope 16. On the other hand, the encapsulated endoscope 16 does not always transmit the radio signal but usually has predetermined intervals. The dummy signal is transmitted through the inspection antenna 33 while the drive states of the antenna selection unit 4 and the like are switched by utilizing the intervals, which allows the performance inspection of the receiving antennas 2a to 2h to be performed while the receiving apparatus 29 is used as a part of the intra-subject information obtaining system. Since the real-time display unit 34 displays the performance inspection result in real time, for example, the subject who is inserted the encapsulated endoscope 16 into the body and uses the receiving apparatus 29 as a part of the intra-subject information obtaining system can make such a response that the broken receiving antenna 2 is changed according to the performance inspection result.

Therefore, in addition to the advantages of the first embodiment, the receiving apparatus 29 according to the second embodiment can prevent the problem that the encapsulated endoscope 16 is inserted into the body plural times due to failure of the receiving antennas 2a to 2h, and the receiving apparatus 29 has the advantage that an increase in burden of the subject can be prevented.

Figure 6:
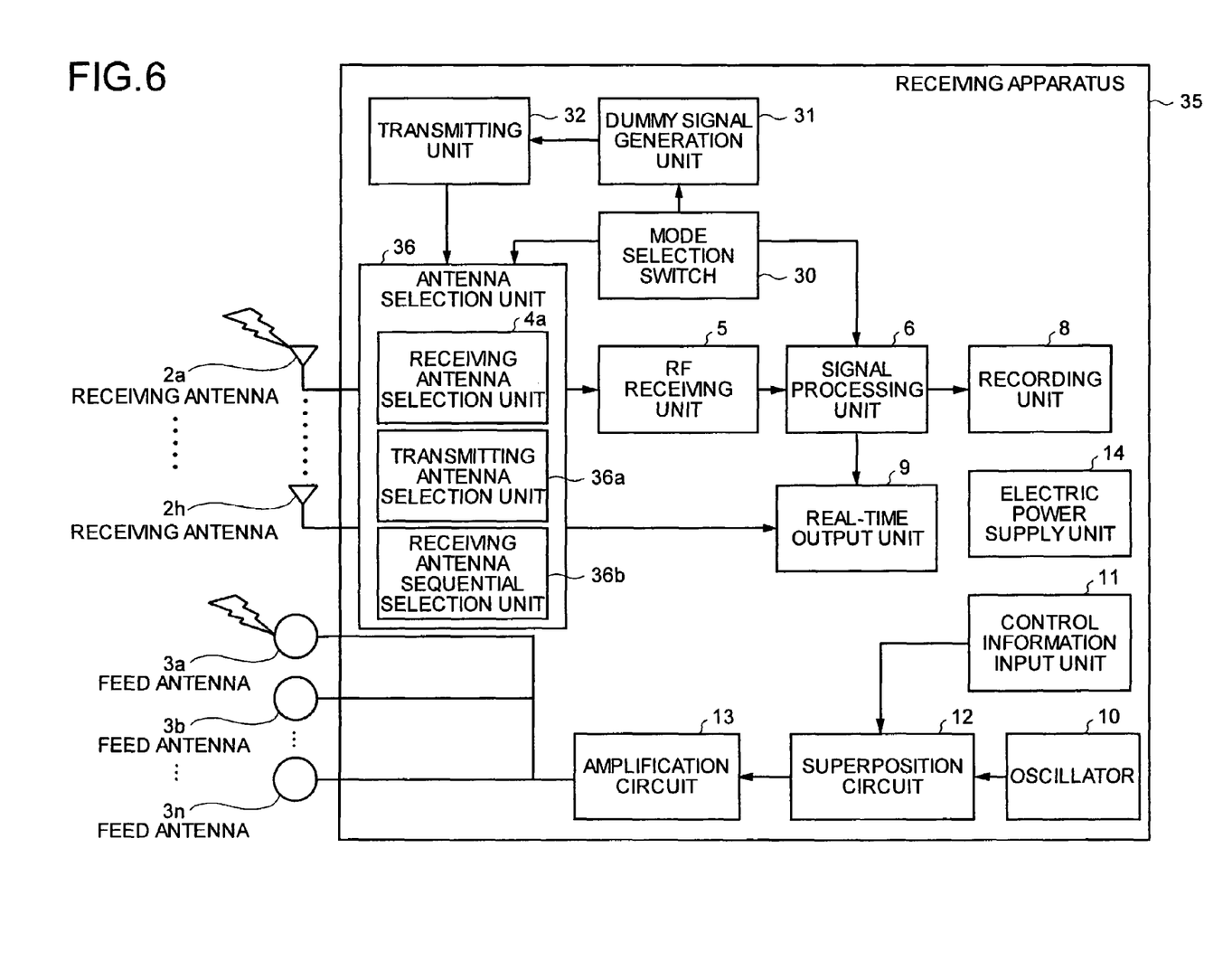
FIG. 6 is a block diagram showing an entire configuration of a receiving apparatus according to a third embodiment.

A receiving apparatus according to a third embodiment will be described. While the receiving apparatus according to the third embodiment is provided with the mechanism which generates the dummy signal in the receiving apparatus like the second embodiment, the receiving apparatus also has the configuration in which a part of the receiving antennas 2a to 2h is caused to function as the transmitting antenna for transmitting the dummy signal in the performance inspection.

FIG. 6 is a block diagram showing an entire configuration of the receiving apparatus according to the third embodiment. As shown in FIG. 6, in addition to the configuration of the first embodiment, a receiving apparatus 35 according to the third embodiment has the configuration in which the mode selection switch 30, the dummy signal generation unit 31, and the transmitting unit 32 are provided like the second embodiment. On the other hand, the receiving apparatus 35 according to the third embodiment has an antenna selection unit 36 instead of the antenna selection unit 4 of the first embodiment and the like. The antenna selection unit 36 includes not only the receiving antenna selection unit 4a but also a transmitting antenna selection unit 36a and a receiving antenna sequential selection unit 36b. The transmitting antenna selection unit 36a selects the dummy signal transmission antenna from the receiving antennas 2a to 2h in the performance inspection of the receiving antennas 2a to 2h. The receiving antenna sequential selection unit 36b sequentially selects the receiving antennas 2 which are not selected by the transmitting antenna selection unit 36a in the performance inspection.

Figure 7:
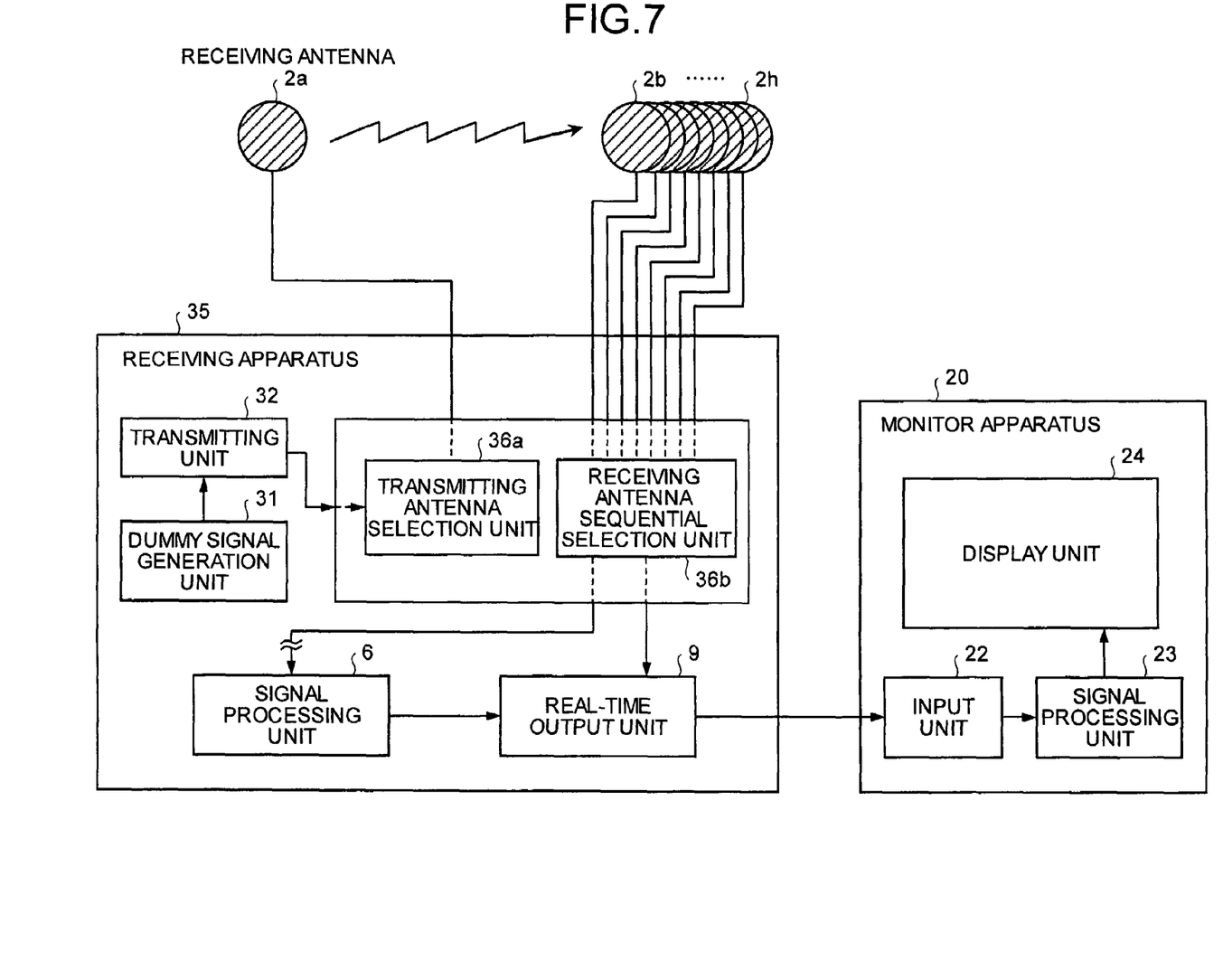
FIG. 7 is a block diagram showing an entire configuration of an inspection system in which the receiving apparatus according to the third embodiment is used.

The operation of the receiving apparatus 35 according to the third embodiment will be described. FIG. 7 is a schematic diagram showing the configuration of the inspection system in which the receiving apparatus 35 according to the third embodiment is used. As shown in FIG. 7, in the performance inspection, the receiving apparatus 35 is used while connected to the monitor apparatus 20 through the real-time output unit 9, and the monitor apparatus 20 has the function of displaying the inspection result through the display unit 24. Similarly to the second embodiment, the receiving apparatus 35 may have the configuration in which the receiving apparatus 35 includes the display function.

In the performance inspection of the receiving antennas 2a to 2h, while the control is performed such that the signal processing unit 6 outputs the data to the real-time output unit 9, the control is performed such that the transmitting antenna selection unit 36a and the receiving antenna sequential selection unit 36b are driven in the antenna selection unit 36. The dummy signal generation unit 31 starts to generate the dummy signal based on the information outputted from the mode selection switch 30, and the dummy signal to which the modulation process and the like are performed is outputted to the antenna selection unit 36 through the transmitting unit 32. Accordingly, in the performance inspection, the receiving apparatus 35 is operated in the mode shown in FIG. 7.

The transmitting antenna selection unit 36a selects an antenna, used for transmitting the dummy signal, from the receiving antennas 2a to 2h. In this selection, an antenna may be selected by a predetermined algorithm, or the receiving antenna may randomly be selected. FIG. 7 shows the case in which the transmitting antenna selection unit 36a selects the receiving antenna 2a as the antenna for transmitting the dummy signal.

On the other hand, the receiving antenna sequential selection unit 36b sequentially selects the receiving antennas 2b to 2h except for the receiving antenna 2a selected by the transmitting antenna selection unit 36a. The selection is similar to the sequential antenna selection unit 4b of the first embodiment, and the receiving antennas 2b to 2h to be inspected are sequentially selected according to the predetermined order irrespective of the receiving intensity of the dummy signal in the receiving antennas 2. The receiving antenna sequential selection unit 36b sequentially selects the receiving antennas 2b to 2h to perform the performance inspection, which enables to determine whether the problem such as the break is generated or not to be determined in the receiving antennas 2b to 2h like the first and second embodiments.

At this point, the performance inspection of the receiving antenna 2a selected by the transmitting antenna selection unit 36a is performed as follows. First, when the dummy signal is surely transmitted from the receiving antenna 2a, the break is not generated in the receiving antenna 2a, so that it can be determined that the performance has no problem. Therefore, when any one of the receiving antennas 2b to 2h can receive the dummy signal, the dummy signal is surely transmitted from the receiving antenna 2a, and it can be determined that the performance of the receiving antenna 2a has no problem.

On the other hand, when any of the receiving antennas 2b to 2h cannot receive the dummy signal, it is difficult to distinguish whether the dummy signal is not received because all the receiving antennas 2b to 2h break down, or the dummy signal is not transmitted because the receiving antenna 2a breaks down. Therefore, when the above inspection result is obtained, in the receiving apparatus 35 according to the third embodiment, the transmitting antenna selection unit 36a selects the receiving antenna different from the receiving antenna 2a, e.g., the receiving antenna 2b, and the performance inspection is performed again by transmitting the dummy signal to the receiving antennas 2a, and 2c to 2h through the receiving antenna 2b.

In the inspection, when the receiving antennas 2b to 2h break down, the dummy signal is not received in any case where one of the receiving antennas 2a and 2c to 2h is selected. On the other hand, when the receiving antenna 2a breaks down, depending on absence or presence of the breakdown of each antenna, the different inspection results are obtained for the receiving antennas 2c to 2h.

Then, the advantage of the receiving apparatus 35 according to the third embodiment will be described. In addition to the advantages similarly to the first embodiment, the receiving apparatus 35 according to the third embodiment has the advantage that the performance inspection can be performed by the simple configuration. That is, the provision of the new transmitting antenna is not required for the purpose of the performance inspection by the configuration in which a part of the receiving antennas 2a to 2h is utilized as the dummy signal transmitting antenna in the performance inspection, so that the complication and the upsizing can be avoided in the configuration of the receiving apparatus 35.

Even if a part of the receiving antennas 2a to 2h is used as the dummy signal transmitting antenna, it is not necessary to particularly change the configuration of the receiving antennas 2a to 2h. As described in the first embodiment, for example, the receiving antennas 2a to 2h include the resonance circuits formed by the loop antennas and the capacitors, and the receiving antennas 2a to 2h receive the radio signal which enters from the outside and has the frequency near the resonance frequency of the resonance circuit. On the other hand, in principle, the receiving antennas 2a to 2h can be caused to function as the wireless transmitting antenna by supplying the electric signal near the resonance frequency from the side of the receiving apparatus 35 to the resonance circuit.

Since the receiving antennas 2a to 2h are formed in order to receive the radio signal transmitted from the encapsulated endoscope 16, the resonance circuit is previously formed such that the resonance circuit has the resonance frequency substantially similar to the radio signal frequency. Further, since the resonance frequencies of the resonance circuit are similar to each other in receiving the radio signal and in transmitting the dummy signal, when the dummy signal is transmitted through, e.g., the receiving antenna 2a, there is no risk that the frequency of the transmitted dummy signal is remarkably different from the resonance frequency of the receiving antennas 2b to 2h. Accordingly, in the third embodiment, it is not necessary that the receiving antennas 2a to 2h are realized by the particular configuration, and any general receiving antenna which receives the radio signal transmitted from the body-insertable apparatus such as the encapsulated endoscope 16 can be inspected in the performance inspection performed by the receiving apparatus 35 according to the third embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

INDUSTRIAL APPLICABILITY

As described above, the receiving apparatus according to the invention is useful when it is used as the radio signal receiving apparatus. Particularly the receiving apparatus according to the invention is preferably used as the receiving apparatus for the radio signal transmitted from the medical instruments such as the body-insertable apparatus.

What is claimed is:

1. A receiving apparatus which is used while connected to a plurality of antennas, the receiving apparatus receiving a radio signal through the antenna to perform a predetermined process to the received radio signal, the radio signal being transmitted from a body-insertable apparatus inserted into a subject and including contents of an image taken by the body-insertable apparatus inside the subject, comprising:
   a mode switching unit that switchably selects one of plural operation modes, the operation modes including at least a normal mode for reception of the radio signal and a performance inspection mode for inspection of performance of the antennas;
   an inspection signal generation unit that is configured to operate in the performance-inspection mode, and generates an inspection radio signal which includes image data similar to the image in the subject taken by the body-insertable apparatus;
   an inspection antenna that is configured to operate in the performance-inspection mode, and transmits the inspection radio signal to the antenna;
   a receiving antenna selection unit that is configured to operate in the normal mode, and selects the antenna which is suitable for reception of the radio signal;
   a sequential antenna selection unit that is configured to operate in the performance-inspection mode, and sequentially selects each of the plurality of antennas;
   a signal processing unit that performs a predetermined process to the radio signal and the inspection radio signal received through the antenna, the antenna being selected by the receiving antenna selection unit or the sequential antenna selection unit, and
   a display unit that displays in real-time a receiving status of the inspection radio signal transmitted from the inspection antenna, wherein
   the performance inspection is performed during a predetermined interval of transmission of the radio signals from the body-insertable-apparatus inserted into the subject.

2. The receiving apparatus according to claim 1, wherein the receiving antenna selection unit appropriately selects the antenna through which receiving intensity of the received radio signal is highest, and
   the sequential antenna selection unit sequentially selects each of the plurality of antennas irrespective of the receiving intensity of the radio signal received through the antenna.

3. The receiving apparatus according to claim 1, wherein the receiving antenna selection unit appropriately selects the antenna through which receiving intensity of the received radio signal is highest, and
   the receiving antenna sequential selection unit sequentially selects the plurality of antennas irrespective of the receiving intensity of the radio signal received through the antenna.

4. The receiving apparatus according to claim 1, wherein the inspection radio signal includes a fixed pattern signal showing a predetermined image.

5. The receiving apparatus according to claim 1, wherein the body-insertable apparatus has an image pickup unit that takes the image in the subject, and
   the inspection radio signal includes an image signal generated by another image pickup unit different from the image pickup unit.

6. The receiving apparatus according to claim 1, further comprising
   a recording unit that is configured to operate in the normal mode, and outputs the received radio signal to a recording medium after the received radio signal is subjected to the predetermined process by the signal processing unit.

7. The receiving apparatus according to claim 1, wherein the display unit includes:
   a mechanism which determines a performance inspection result, and
   an LED which displays a pattern corresponding to the determined performance inspection result.

* * * * *